United States Patent
Lyu et al.

(10) Patent No.: US 6,958,162 B2
(45) Date of Patent: Oct. 25, 2005

(54) HERBAL COMPOSITION FOR TREATING ALLERGIC DISORDERS AND METHOD FOR MAKING THE SAME

(75) Inventors: Rong-Ming Lyu, Hsinchu (TW); I-Hong Pan, Hsinchu (TW); Jir-mehng Lo, Hsinchu (TW); Sue-Fen Jiang, Hsinchu (TW); Sheau-Ni Su, Hsinchu (TW); Nai-Yun Hsu, Hsinchu (TW); Shih Cheng Shen, Hsinchu (TW); Hsin-Chieh Wu, Hsinchu (TW); Lain-Tze Lee, Hsinchu (TW); Yih-Loong Lai, Yunghe (TW); Jaw-Ji Tsai, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 10/608,005

(22) Filed: Jun. 30, 2003

(65) Prior Publication Data

US 2004/0265402 A1 Dec. 30, 2004

(51) Int. Cl.⁷ .............................................. A61K 35/78
(52) U.S. Cl. ........................ 424/725; 424/773; 514/826
(58) Field of Search ................................ 424/725, 773; 514/826

(56) References Cited

U.S. PATENT DOCUMENTS

| | | | |
|---|---|---|---|
| 5,503,810 A | * | 4/1996 | Chang ........................ 422/235 |
| 6,093,403 A | * | 7/2000 | Huo et al. .............. 424/195.15 |
| 2002/0031559 A1 | * | 3/2002 | Liang et al. ................. 424/725 |
| 2004/0105902 A1 | * | 6/2004 | Chen .......................... 424/756 |

* cited by examiner

Primary Examiner—Christopher R. Tate
(74) Attorney, Agent, or Firm—Bacon & Thomas, PLLC

(57) ABSTRACT

Pharmaceutical compositions for treating immunological disorders and the preparing method of the same are disclosed, which include alcohol extracts of *Radix Dioscorea, Rhizoma Alismatis, Poria cocos* (schw) Wolf, and *Scutellaria Baicalensis*. The compositions are manufactured by novel procedures consisting of decocting using specific concentration ranges of alcohol, filtering, regulating pH value, purifying, concentrating, proportionally mixing, and making a granule powder from lyophilized extract. This invention used both in vitro and in vivo assays to evaluate therapeutic effects of specific combination of herbal plant extracts. The combination of herbal extracts has been able to maximize the anti-inflammatory activity and regulate the secretion of cytokines such as eotaxin and IL-4. When the pharmaceutical composition of the present invention is used for asthma, it can relieve coughs, resist airway allergic inflammation reactions, improve the pulmonary functions, reduce allergen specific IgE in bloods, stabilize elasmatoblasts, and stop the attacks from asthma.

15 Claims, 14 Drawing Sheets

HERBAL COMPOSITION FOR TREATING ALLERGIC DISORDERS AND METHOD FOR MAKING THE SAME

BACKGROUND OF THE INVENTION

1. Field of the Invention

The present invention relates to a pharmaceutical composition for treating allergic disorders and method for making the same, and more particularly, to the herbal pharmaceutical composition for treating allergic asthma and a method for making the composition.

2. Description of Related Art

It is known that allergen-induced disorders, such as asthma, are still one of the serious health problems in the world. Recently, the onset of these allergic-related immunological disorders has shifted to the younger population. In other words, more children and adolescents have developed symptoms of allergen-induced immunological disorders. Many doctors and scientists believe that the early onset of allergen-related immunological disorders is accordingly linked to increasing environmental pollution.

While the percentage of the affected population and severity of the diseases are rising, the precise factors responsible for the increase of the population are not entirely clear. Therefore, our current methods for treating asthma still primarily depend on empirical and serendipitous findings rather than on a scientific fundamental approach. At present, anti-asthma medication has focused largely on either improving existing therapies (e.g. antileukotriene) or the prevention and reversal of inflammation (e.g. steroid inhalants) by inhibiting the inflammatory cytokines. However, it is found that those children having history of eczema and hay fever are also very vulnerable to asthma attack and this has raised the question "Should people with mild asthma whose symptoms occur more than occasionally take anti-asthma medications on a daily basis and last for years?" In response to such a question, it is worthy to test the effects of the traditional Chinese herbs, for which many documents indicate the benefits in reference to allergic diseases such as atopic dermatitis.

The traditional Chinese herbs have long been used for treating atopic dermatitis and asthma. It was revealed that the conditions of most patients could be improved in general by using traditional Chinese herbal medicines but the reason why patients cannot be totally and permanently cured is not clear. Some herbal medicines appear to be effective in the short term and with few occurrences of adverse effects, but the long-term effects for preventing disease progression are still waiting for more scientific studies. Therefore, further studies of traditional Chinese herbs should be carried out. The following references indicate the herbal medicines have functions of immunomodulation, but most of them obviously have unstable factors and should be intensively studied.

For example, U.S. Pat. No. 6,503,542 disclosed a pharmaceutical composition, which comprises water extracts of *Tuber Ophiopogon, Tuber Pinelliae, Radix Glycyrrhizae,* and *Radix Pancis Quinquefoli,* and 50% alcohol extraction of *Herba Tridacis procumbentis* for *Rhinitis*. The recipe contained five herbs and retained a good effect of anti-inflammation. However, it is not easy to control the long-term therapeutic effect because this formulation has only a temporary symptom-releasing function.

WO 02/78723 A1 disclosed a pharmaceutical preparation of Chinese herbs which consists of kidney-fortifying and anti-asthma herbs, wherein said Chinese herbs comprise *Ferilla Frutescens, Prunus Armeniaca, Glycyrrhiza Uralensis, Scutellaria Baicalensis, Coptis Chinesis, Tusilago Farfara, Stemona Sessilifolia, Fritllaria Cirrhosa, Pheretima Aspergillum, Psoralea Corylifolia, Codonopsis Pilosula, Hordeum Vulgara, Massa Fermentata Medicalis, Schisandra Chinensis,* and *Gypsum*. The quality of this herbal extract is hard to be controlled because this recipe consists of fifteen kinds of herbs. A significant effect of drug-drug interaction is hard to be appreciated.

WO 02/32440 disclosed a *Murraya koenigii* extract for treating asthma. GB 2274059 disclosed a pharmaceutical composition comprising peony for asthma relief. Those disclosures use the extract of a single plant to treat or provide relief from acute asthma, but cannot maintain a long-term curative effect.

Therefore, it is desirable to provide a much simpler composition and manufacture methods, which prevent the active ingredients from changing before use in treating illness, improve the long-term therapeutic effects for treating immunological disorders, and/or obviate the aforementioned problems.

There are a few traditional Chinese herbs, which have a strong anti-inflammatory property and may be good for treating immunological disorders. For example, the effects of *Scutellaria Baicalensis* as an anti-inflammatory have been documented in ancient China since before $2^{nd}$-century AD and this herb is one of the main remedies for diseases occurring in "hot and damp" conditions, such as dysentery and diarrhea. However, there are no descriptions about how to manufacture the herb into homogenous powders for long-term storage and how to use it specifically for the treatment for allergic asthma. Therefore, this disclosure contains novel processes with minimum procedures to generate a therapeutic composition that combines *Scutellaria Baicalensis* with three other herbal extracts to reveal very good efficacy in vitro and in vivo studies. In other words, the combination of *Scutellaria Baicalensis* with three other herbal extracts does offer the benefits of extending the stability of several active components, exhibit efficacy on anti-allergic asthma, and decrease the toxicity of drugs in a human body.

SUMMARY OF THE INVENTION

The object of the present invention is to provide a pharmaceutical composition to alleviate the symptoms of allergic asthma, and to treat patients with allergic asthma effectively.

To achieve the object mentioned above, the pharmaceutical composition for treating allergic asthma of the present invention comprises alcohol extracts of *Radix Dioscorea, Rhizoma Alismatis, Poria cocos* (schw) Wolf, and *Scutellaria Baicalensis*. The preferred weight ratio of *Radix Dioscorea, Rhizoma Alismatis, Poria cocos* (schw) Wolf, and *Scutellaria Baicalensis* is around 1:1–2: 0.5–2: 1–3. The *Radix Dioscorea* can be chosen from a large variety of species. The best effect comes from either *Dioscorea opposita Thunb* or *Dioscorea alata* L, which have been collected and identified by experts among assignee (the Industrial Technology Research Institute in Taiwan). Compositions extracted from both species of *Dioscorea* exhibited equal potency in inhibition of cytokines, such as IL-4 and TNF-alpha released from cells, which is identified in the in vitro assays as described in the following section of examples.

The present invention also provides a method for preparing a pharmaceutical composition composed of the alcohol extracts of *Radix Dioscorea, Rhizoma Alismatis, Poria cocos* (schw) Wolf, and *Scutellaria Baicalensis*. The method comprises the following steps: extracting *Radix Dioscorea, Rhizoma Alismatis, Poria cocos* (schw) Wolf, and *Scutellaria Baicalensis* in alcohol separately to form the alcohol extracts of *Radix Dioscorea, Rhizoma Alismatis, Poria cocos* (schw) Wolf, and *Scutellaria Baicalensis*; filtering and concentrating each of said alcohol extracts to form condensates of *Radix Dioscorea, Rhizoma Alismatis, Poria cocos* (schw) Wolf, and *Scutellaria Baicalensis*; and mixing said condensates of *Radix Dioscorea, Rhizoma Alismatis, Poria cocos* (schw) Wolf, and *Scutellaria Baicalensis* together.

The present invention further provides another method for preparing a pharmaceutical composition composed of water or alcohol extracts of *Radix Dioscorea, Rhizoma Alismatis, Poria cocos* (schw) Wolf, and *Scutellaria Baicalensis*. The method comprises the following steps: mixing *Radix Dioscorea, Rhizoma Alismatis, Poria cocos* (schw) Wolf, and *Scutellaria Baicalensis* to form a mixture; extracting said mixture in water or alcohol to form an extract of *Radix Dioscorea, Rhizoma Alismatis, Poria cocos* (schw) Wolf, and *Scutellaria Baicalensis*; and filtering and concentracting said extract to form a condensate of *Radix Dioscorea, Rhizoma Alismatis, Poria cocos* (schw) Wolf, and *Scutellaria Baicalensis*.

Preferably, the aforesaid extraction is performed in alcohol. Most preferably, the extraction is performed in 0% to 95% alcohol.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
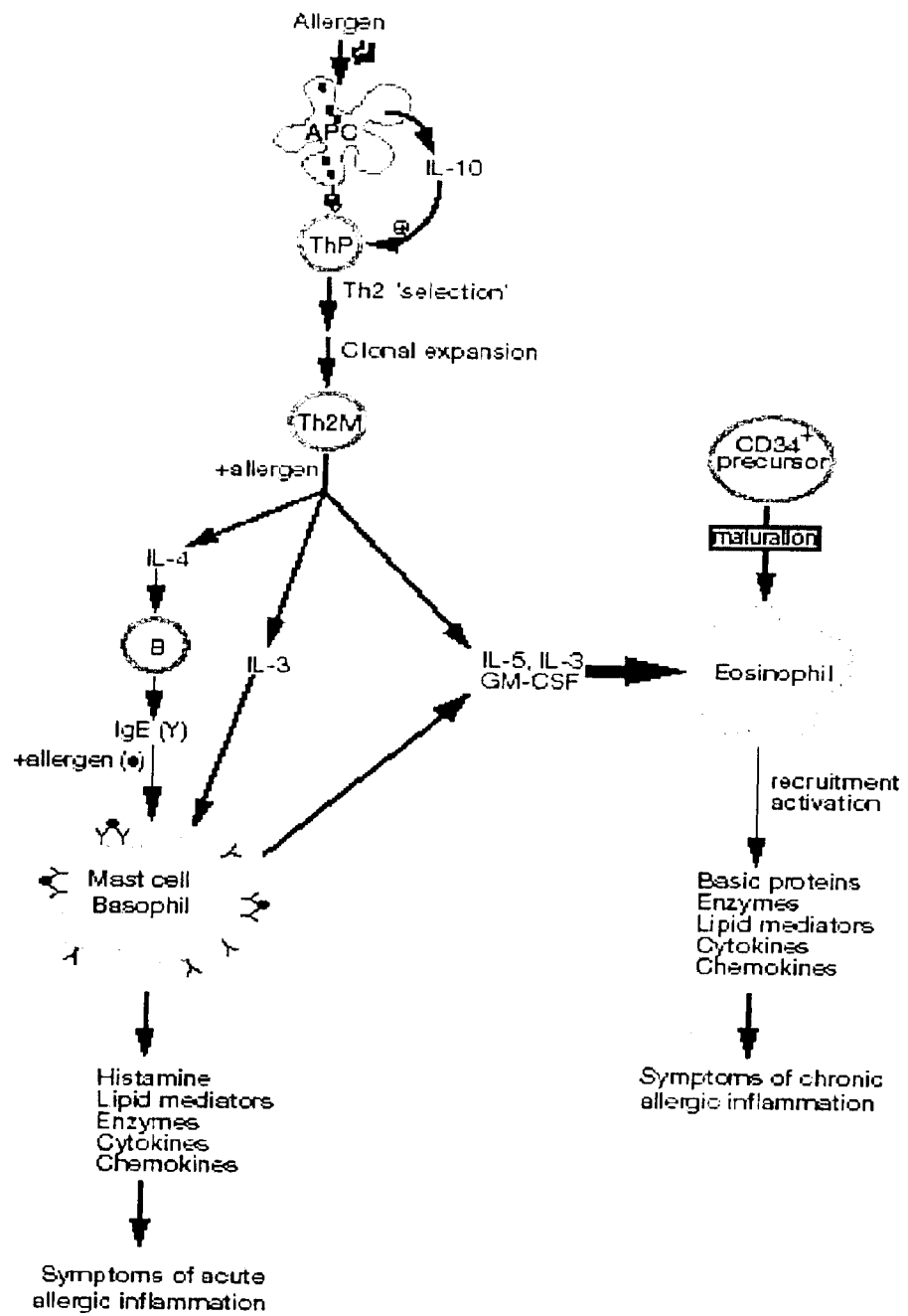
FIG. 1 is a schematic route of a possible mechanism of allergic asthma (excerpted from P. G. Holt, C. Macabas, P. A. Stumbles and P. D. Sly in 'Nature' 402, 12–17(1999)); wherein IL-4 is the major cytokine released from Th2 cells and leukotrienes are important lipid mediatore in both acute and chronic allergic inflammation.

Antigen or allergen-mediated asthma is a respiratory disease primarily due to chronic inflammatory reaction. The inflammatory reaction is mediated by the release of inflammatory factors, such as platelet activation factor, histamine, prostaglandin, and leukotriene, from the cells. Inflammatory reaction stimulates antigenic response in T lymphocytes (T cells), particularly CD4+ cells. There are two types of CD4+ cells. T helper 1 (Th1) type of CD4+ cells secretes cytokine such as IFN-γ. T helper 2 (Th2) type of CD4+ cells secretes cytokines such as interleukin-4 (IL-4) and IL-5. Analysis of blood, bronchoalveolar lavages and bronchial mucosal biopsies from patients having allergic asthma reveal a predominant activation of Th2 cells. The allergen stimulates the Th2 cells to produce excess IL-4, which in turn induces the production and secretion of IgE from B lymphocytes as shown in FIG. 1. The release of eotaxin from tracheal epithelium also recruits a lot of eosinophils to this inflammatory region. Pharmaceutical compositions of the present invention can prevent the release of inflammatory factors and IL-4.

The following examples are illustrative, and should not viewed as limiting the scope of the present invention.

EXAMPLE 1

Preparation of the Pharmaceutical Composition TCM-A

A pharmaceutical composition is prepared as the following five steps:

(1) 400 g of the tubers or roots of *Radix Dioscorea*, 300 g of *Poria cocos* (schw) Wolf, and 500 g of *Scutellaria Baicalensis* were separately cut into small pieces.

(2) Each of *Radix Dioscorea* and *Poria coca* (schw) Wolf was submerged in 2000 ml water, and *Scutellaria Baicalen-*

*sis* was submerged in 70% alcohol for half an hour. Each solution was heated to 85 degrees C. for about 60 minutes. Then extracts of *Radix Dioscorea, Poria cocos* (schw) Wolf, and *Scutellaria Baicalensis* were obtained respectively.

(3) After each extract was cooled, the extract was separately filtered through a sieve (approximately 100 mesh). The filtrate was collected, and then condensed through condensation at a temperature ranging from 50 to 60° C. under a vacuum condition (at 30 torr). A liquid condensate was obtained for each herb.

(4) An adequate amount of carboxyl methylcellulose (as excipient) was added before freeze-drying each of the condensates, and then granulated to produce individual granules.

(5) The individual granules were mixed together to form mixed granules, named TCM-A, and encapsulated.

EXAMPLE 2

Preparation of the Pharmaceutical Composition TCM-B

A pharmaceutical composition is prepared as the following five steps:

(1) 400 g of the tubers or roots of *Radix Dioscorea*, 400 g of *Rhizoma Alismatis*, 300 g of *Poria cocos* (schw) Wolf, and 500 g of *Scutellaria Baicalensis* were separately cut into small pieces.

(2) Each of *Radix Dioscorea* and *Poria coca* (schw) Wolf was submerged in 2000 ml water, *Rhizoma Alismatis* was submerged in 2000 ml of 50% alcohol, and *Scutellaria Baicalensis* was submerged in 70% alcohol for half an hour. Each solution was heated to 85 degrees C. for about 60 minutes. Then extracts of *Radix Dioscorea, Rhizoma Alismatis, Poria cocos* (schw) Wolf, and *Scutellaria Baicalensis* were obtained respectively.

(3) After each extract was cooled, the extract was separately filtered through a sieve (approximately 100 mesh). The filtrate was collected, and then condensed through condensation at a temperature ranging from 50 to 60° C. under a vacuum condition (at 30 torr). A liquid condensate was obtained for each herb.

(4) An adequate amount of carboxyl methylcellulose (as excipient) was added before freeze-drying each of the condensates, and then granulated to produce individual granules.

(5) The individual granules were mixed together to form mixed granules, named TCM-B, and encapsulated.

EXAMPLE 3

Preparation of the Pharmaceutical Composition TCM-C

A pharmaceutical composition is prepared as the following steps:

(1) 400 g of the tubers or roots of *Radix Dioscorea*, 400 g of *Rhizoma Alismatis*, 300 g of *Poria cocos* (schw) Wolf, and 500 g of *Scutellaria Baicalensis* were separately cut into small pieces.

(2) The first three herbs were submerged together in 2000 ml of 50% alcohol, while *Scutellaria Baicalensis* was submerged in 70% alcohol solution. The alcohol solutions were heated for about 30 minutes and then the alcohol extract of the mixture of *Radix Dioscorea, Rhizoma Alismatis, Poria cocos* (schw) Wolf, and *Scutellaria Baicalensis* was obtained.

(3) After the extracts were cooled, the extracts were filtered through a sieve (approximately 100 mesh) and mixed to form a filtrate. The filtrate was condensed through condensation at a temperature ranging from 50 to 60° C. under a vacuum (at 30 torr). Then a liquid condensate was obtained and freeze-dried under a vacuum to form a powder.

(4) An adequate amount of carboxyl methylcellulose or $Ca_3(PO_4)_2$ (as excipient) was added to the dry powder and mixed homogeneously. The whole mixture was granulated by a freezing-drying method to produce a granule, named TCM-C.

(5) The granule was encapsulated under a dry place and bottled with nitrogen gas.

EXAMPLE 4

Preparation of the Pharmaceutical Composition TCM-D

A pharmaceutical composition is prepared as the following steps:

(1) 400 g of the tubers or roots of *Radix Dioscorea*, 400 g of *Rhizoma Alismatis*, 300 g of *Poria cocos* (schw) Wolf, and 500 g of *Scutellaria Baicalensis* were separately cut into small pieces and then mixed together to form a mixture.

(2) Mixture of the four herbs was submerged in 6000 ml of 50% alcohol. The alcohol solution was heated for about 60 minutes and then the alcohol extract of the mixture of *Radix Dioscorea, Rhizoma Alismatis, Poria cocos* (schw) Wolf, and *Scutellaria Baicalensis* was obtained.

(3) After the extract was cooled, the extract was filtered through a sieve (approximately 100 mesh). The filtrate was collected, and then condensed through condensation at a temperature ranging from 50 to 60° C. under a vacuum (at 30 torr). A liquid condensate was obtained and freeze-dried under a vacuum.

(4) An adequate amount of carboxyl methylcellulose or $Ca_3(PO_4)_2$ (as excipient) was added to the dry powder and mixed homogeneously. The whole mixture was granulated by a freezing-drying method to produce a granule, named TCM-D

EXAMPLE 5

In Vitro Assay

Figure 2A:
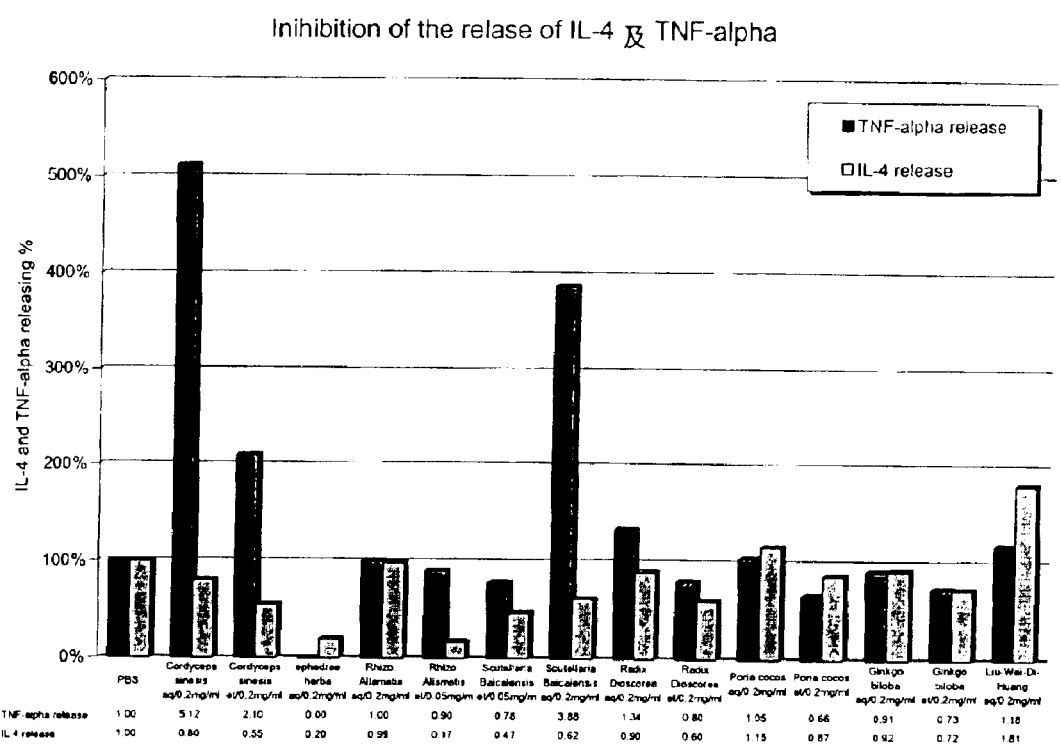
FIG. 2a shows a graphic result of the in vitro test for each composition to inhibit the release of IL-4 and TNF-alpha from cell lines of EL-4 and THP-1 cells. The symbol "aq" in the text at the bottom of the figure represents the water extract of that herb. The symbol "et" in the text at the bottom of the figure represents the ethanol extract of that herb.
Figure 2B:
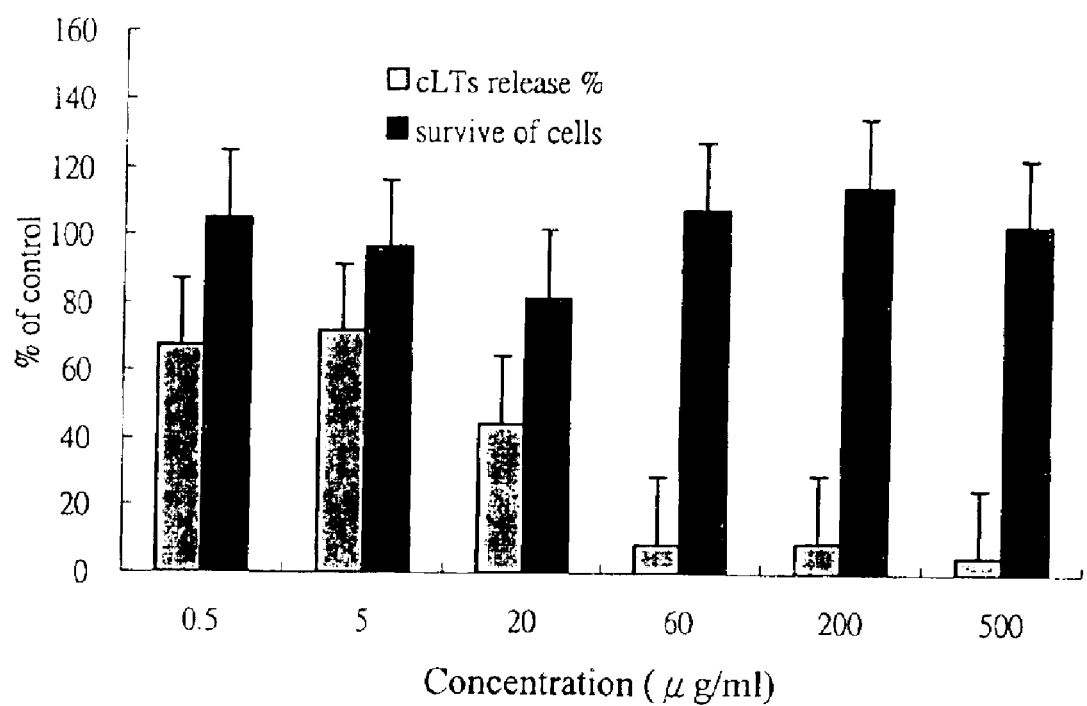
FIG. 2b shows a graphic result of the in vitro test of different concentration of TCM-B to inhibit the release of cysteinyl-leukotrienes and their cytotoxicity of RBL-1 cells.

The inhibition to IL-4 of several herbs is tested. As shown in FIG. 2*a*, 2*b* and FIG. 3, it is clear that *Radix Dioscorea, Rhizoma Alismatis, Poria cocos* (schw) Wolf, and *Scutellaria Baicalensis* can inhibit the release of IL-4, TNF-alpha and eotaxin.

(A) Inhibition of Cytokine (IL-4, TNF-Alpha) Produced from Cultured Cell Lines

During the day of experiment, the herbal drug was diluted in the cell culture medium to the end point (0.5 μg/ml, 5 μg/ml, or as appropriate). The ability of each herbal composition and its mixtures to affect the production of IL-4, TNF-alpha, and cLT was measured.

A1: Measurements of IL-4 with EL-4 Cell Lines:

The mouse thymoma cell lines, EL-4 were incubated with each composition or mixture for 2 hours before it was stimulated by 100 ng/ml of A23187 and PMA. Samples of tissue culture medium were collected at the end of 24 hours incubation and stored at −70 degrees C. prior to assay.

Cytokine measurements were carried out using the commercially available ELISA assay kit (R&D Systems, Minneapolis, Minn.) in accordance with the supplier's protocols. In brief, 100 μl of the assay buffer supplied was added to each of the wells of a micro-titer plate containing pre-bound anti-cytokine antibody, followed by 100 μl of a standard or sample solution, diluted appropriately for the concentration range measured. All incubations were carried out at 37 degrees C. After two hours incubation, the plates were washed four times with a wash buffer, and the second antibody, Detection Antibody, was added with 1:200 in Reagent Diluent to each well. The plates were sealed and incubated for 2 hours. Then, Streptavidin-HRP diluted with 1:200 in Reagent Diluent was added to each well and incubated for 20 minutes at room temperature in the dark. After aspirating and washing off non-biding streptavidin-HRP, 100 μl of Substrate Solution (TMB) was added into each well. The plates were incubated for 30 minutes at room temperature in the dark. After 20 minutes incubation, the reaction was terminated by addition of 50 μl 2N $H_2SO_4$ to each well. Optical sensitivity was determined at 450 nm using a Molecular Devices of micro-titer plate reader.

The measurement procedures of TNF-alpha were exactly the same as those described in IL-4 measurement except that the cell was cultured with THP-1 instead of EL-4 cells and the activity was measurement with antibody against TNF-alpha.

As shown in FIG. 2a, basal level of IL-4 and TNF-alpha decreased markedly (90% of TNF-alpha with 17% of IL-4, and 78% TNF-alpha with 47% of IL-4, respectively) owing to the inhibition of ethanol extract of *Rhizoma Alismatis* and *Scutellaria Baicalensis*. At a concentration of 0.2 mg/ml, ethanol extract of *Radix Dioscorea* inhibits IL-4 for 40% and TNF-alpha for 20%, respectively. Most of the extracts inhibit the production of cytokine depending on dosage used, while cytokine concentration decreased as medium, protein degradation increased. At least in part, decreasing cytokine production is resulted from the decreasing of EL-4 and THP-1 proliferation in vitro as well as the immunosuppressive effect of the extract of herbal composition in vivo.

The procedures were the same as described above as in the measurement of IL-4, except that the cell line used was THP-1 and culture medium was RPMI. Supernatants in the wells were TNF-alpha antibody, which is screened by ELISA to quantify secreted TNF-alpha.

A2: The Cells in Each Well were Measured Again with MTT to Detect the Cytotoxicity of Each Herbal Drug Applied into Each Well.

Potential cytotoxicity of each composition and mixture were measured by detecting MTT reducibility of EL-4 cells. MTT (3', 5'-Dimethylthiazol-2yl-2,5-diphenyltetrazolium bromide), a yellow compound, is reduced by mitochondria's enzymes to form a purple crystalline product (formazan), and provides or induces cellular compatibility or cytotoxicity.

The cytotoxicity EL-4, THP-1, and RBL-1 cells were assayed by the measurement of IL-4, TNF-alpha, and cysteinyl-leukotriene (c-LT) as described above. A stock solution of MTT (Sigma Chemical Co., St. Louis, Mo.) 5 mg/ml in phosphate buffer saline, pH 7.4, was prepared. After 21 hours incubation under identical conditions, 5 μl of MTT solution was added into each culture well. After another 4 hours incubation, the interaction was terminated by adding DMSO. After mixing and incubating at 25 degrees C., the optical density of the sample was determined with Molecular Device of micro-titer plate reader under 560 nm. Data were expressed with the ratio of the sample optical density to untreated controls.

A3: Measurement of Cysteinyl-Leukotrienes (c-LTs) with RBL-1 Cell Line:

The RBL-1 (rat basophilic leukemia-1 cells) were stimulated with 0.1 μg/ml Retinoic acid for 16 hours to activate intracellular LTC4 synthetase. Then, a herbal composition mixture was added into the culture medium and incubated for 2 hours at 37 degrees C. After that 10 μM of A23187 was added to stimulate the production of c-LT. The experiment was terminated after 15 minutes of being incubated with A23187, and 100 μl of supernatant was collected. The concentrations of c-LTs were measured with the cell supernatant fluids using a commercially available ELISA kit (Cayman Chemical, Michigan, USA) following the manufacturer's instruction.

Figure 4A:
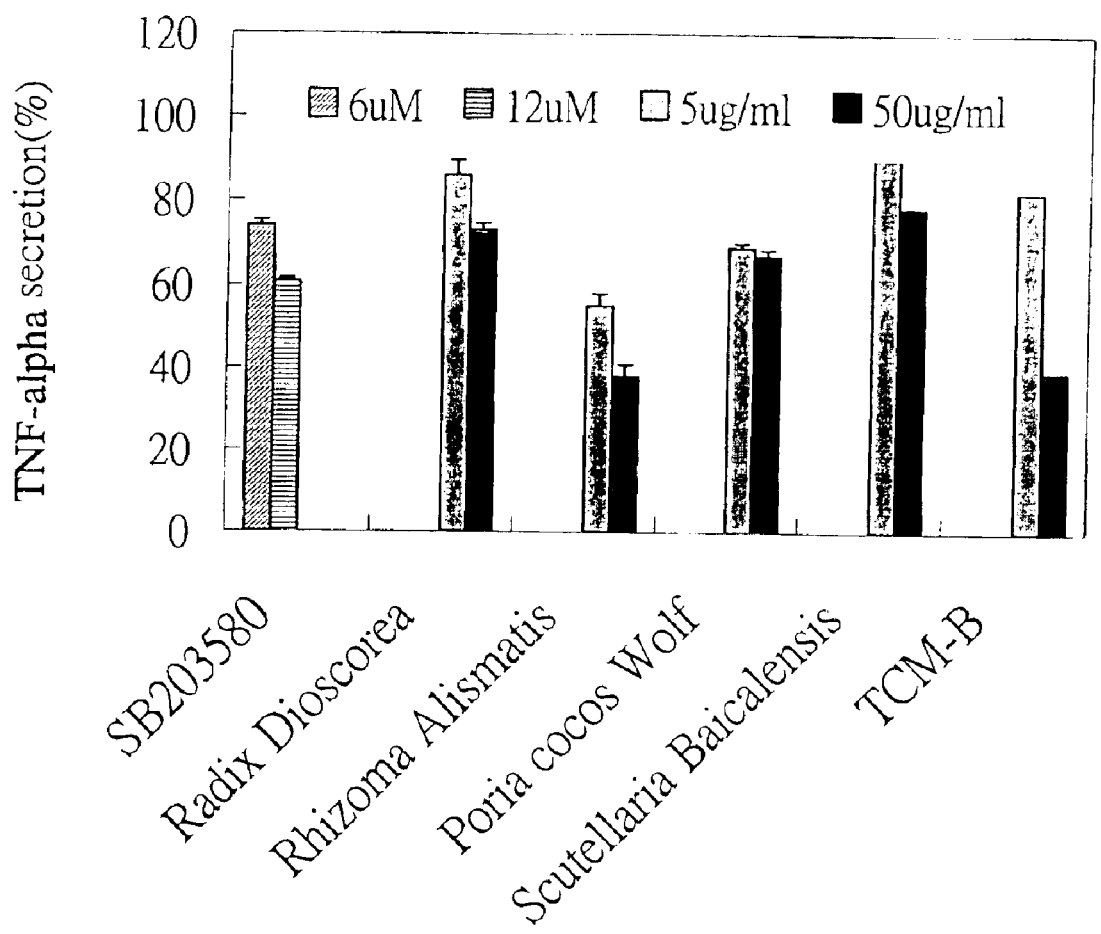
FIG. 4a shows a graphic result of the in vitro test for each composition and mixture TCM-B to inhibit the TNF-alpha released from peritoneal macrophage.

A4: Measurement of TNF-Alpha Using Mouse Peritoneal Macrophages:

Peritoneal macrophages were obtained from male Balb/c mice (6 to 8 WEEKS OLD), which were previously i.p injected with 3% Brewer thioglycolate medium. Peritoneal cells were collected 7 days later by peritoneal lavage with ice-cold RPMI-1640 medium with 10% FBS and incubated for 2 hours at 37 degrees C. The non-adherent cells were removed by washing and used for TNF-alpha assays. In this assay, a specific inhibitor for P-38 MAP kinase—SB203580—was a positive control in each experiment. As shown in FIG. 4a, the inhibition by SB203580 also indicates the response of cells to LPS.

(B) Inhibition of Eotaxin Secretion from Human BEAS-2B Cells

This experiment used BEAS-2B cells which were obtained from American Type Culture Collection (ATCC). BEAS-2B epithelial cells were isolated from normal human bronchial epithelium obtained from autopsies of non-cancerous individuals.

Figure 3A:
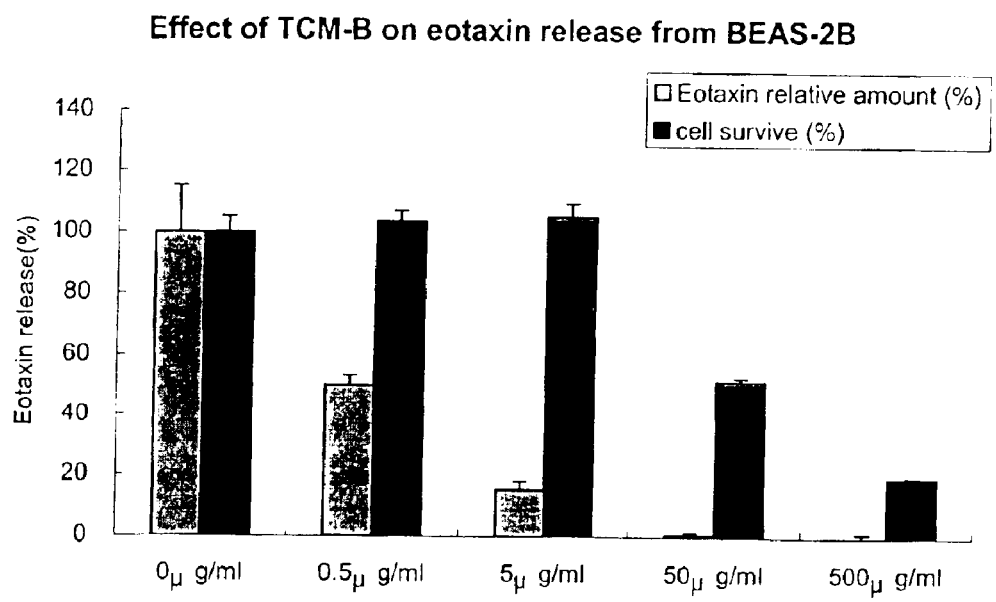
FIG. 3a shows a graphic result of the in vitro test for different concentration of TCM-B to inhibit the release of eotaxin and the cell survival rate (cytotoxicity) for BEAS-2B cells measuring by MTT assays.

The assay included two parts, a cytotoxicity test and an eotaxin secreting suppression test. Each pharmaceutical composition and mixture was tested for its cytotoxicity firstly as described herein, and expressed in terms of the percentage of cell survival rate. As shown in FIG. 3a, the higher the percentage means the substance being tested is not toxic to the cells. Usually, a nontoxic herbal mixture has a cell survival ratio higher than 80%, and is chosen for the inhibition of eotaxin releasing assay.

In the eotaxin releasing assay, BEAS-2B cells were seeded with DMEM/F12 in a 96-well micro-titer plate at 37 degrees C. for one day. The BEAS-2B cells were cultivated in a culture medium with the indicated concentrations of the herb mixture for 2 hours at 37 degrees C. before adding 100 ng/ml of IL-13 and 100 ng/ml of TNF-α in 20 μl PBS to stimulate BEAS-2B for 72 hours at 37 degrees C. After that, 100 μl of the cell supernatants were collected to quantify the amounts of eotaxin by ELISA. The amount of eotaxin released in the medium without the presence of any herbal mixture or pituitary adenylate cyclase polypeptides (PACAP) was taken for the background level. The suppression of eotaxin released by PACAP in a concentration of 0.001 μM was a positive control to validate the experiment results each time.

Figure 3B:
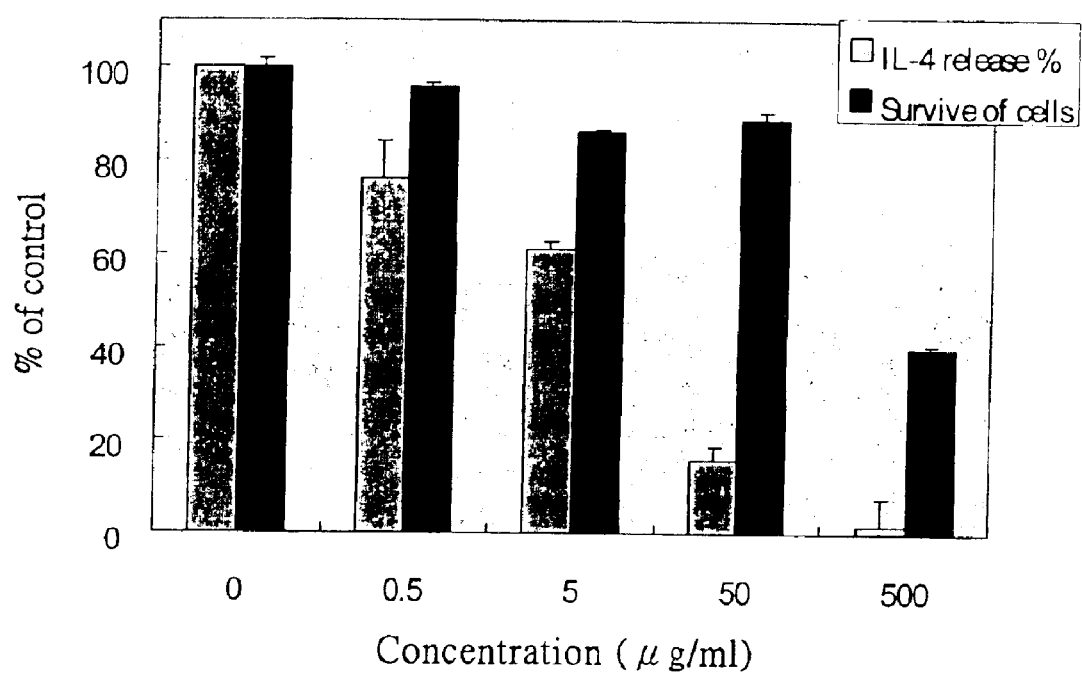
FIG. 3b shows a powder of TCM-B which contains 36% of starch and 1.9% of $Ca_3(PO_4)_2$ and was tested for effect of IL-4 released from EL-4 cells. The abscissa represents the concentration of this powder, and the excipient, starch and $Ca_3(PO_4)_2$, have been tested and did not have any effect on the IL-4 released from EL-4 cells.
Figure 3C:
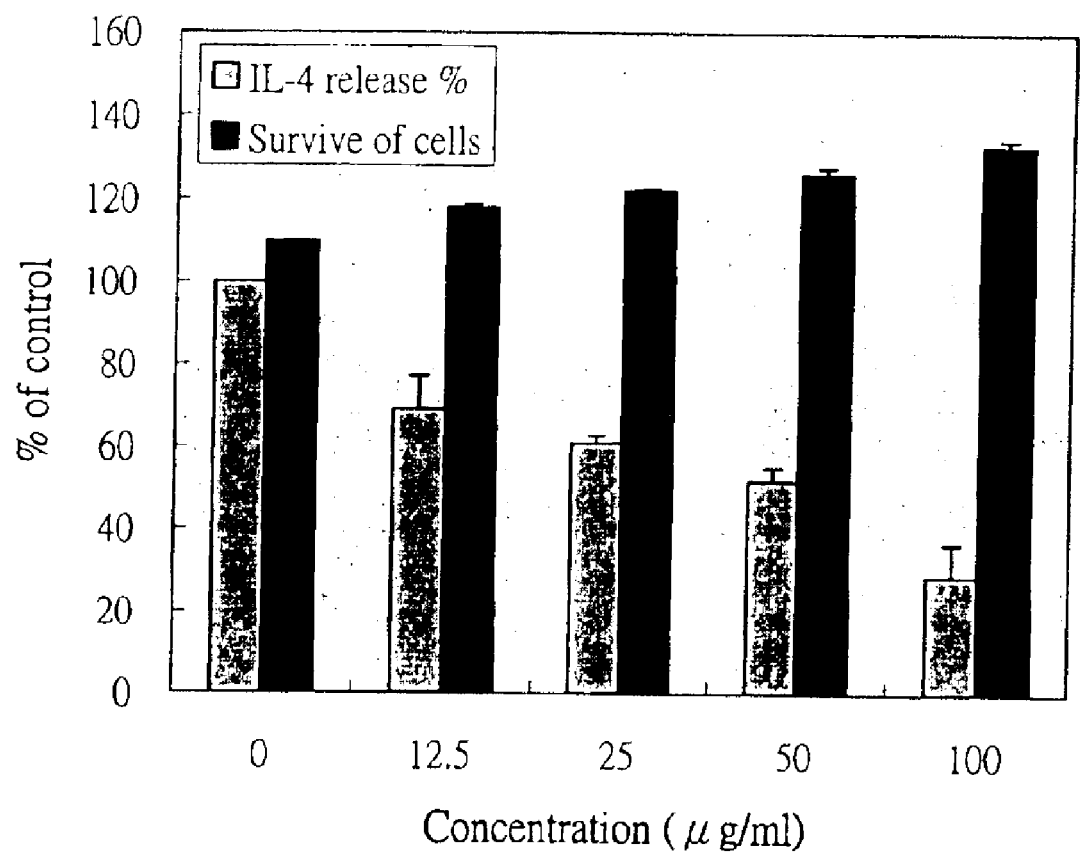
FIG. 3c shows the herbal extract powder containing TCM-B and excipients maintained an equivalent inhibitory effect on IL-4 released from EL-4 cells.

The data listed in FIG. 3a shows that TCM-B containing the herbal mixture of *Radix Dioscorea, Rhizoma Alismatis, Poria cocos* (schw) Wolf, and *Scutellaria Baicalensis* at 0.5 μg/ml can inhibit eotaxin released from BEAS-2B cells significantly and have no cytotoxicity. The data of FIG. 3b shows the inhibition TCM-B on the IL-4 released from EL-4 cells. This inhibitory effect is a dose dependent relationship, although at the highest dose, 500 μg/ml, it affects the viability of EL-4 cells. A powder of TCM-B containing 36% of starch and 1.9% of $Ca_3(PO_4)_2$ was tested on its effect of IL-4 released from EL-4 cells. This study also examines the effect of common excipients such as starch and $Ca_3(PO_4)_2$ on the IL-4 release from EL-4. The result showed that excipients, i.e. starch and $Ca_3(PO_4)_2$, do not have any effect on the IL-4 released from EL-4 cells. The powder, which contains TCM-B and excipients, maintained an equivalent inhibitory effect on IL-4 released from EL-4 cells, as shown in FIG. 3c. Therefore, starch and $Ca_3(PO_4)_2$ were used at the stage of granulation of herbal extract powder.

Figure 4B:
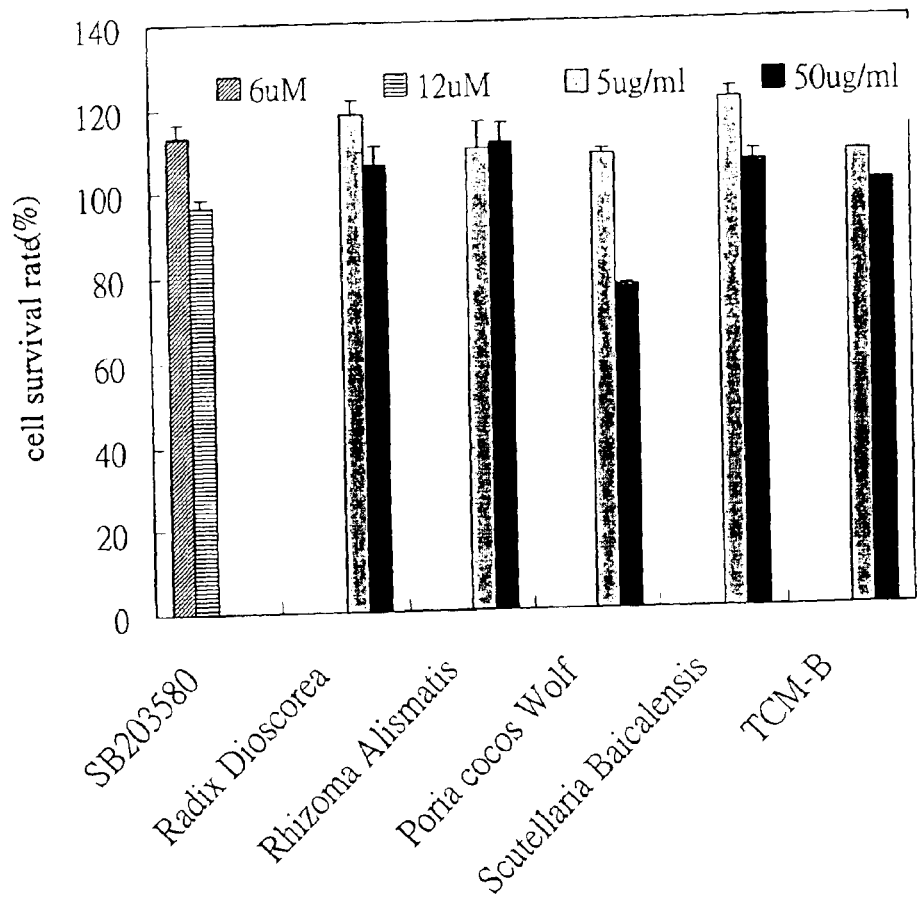
FIG. 4b shows the cytotoxicity of each composition and mixture TCM-B as measured by MTT assays in peritoneal macrophage.

As shown in FIG. 4a, TCM-B at concentration of 50 µg/ml can inhibit the TNF-alpha secretion from peritoneal macrophage. The inhibitory effect of TCM-B is less than that shown by the same amount of extract of *Rhizoma Alismatis*. However, in FIG. 4b, the herbal extract of *Rhizoma Alismatis* at 50 µg/ml has a certain degree of cytotoxicity to peritoneal macrophages. The same situation of increased cell survival was observed from the assays to inhibit eotaxin released from BEAS-2B cells. Therefore, the combination of *Radix Dioscorea, Rhizoma Alismatis, Poria cocos* (schw) Wolf, *Scutellaria Baicalensis* to produce TCM-B, not only can maintain its inhibition ability on TNF-alpha release, but also decreases the cytotoxicity of TCM-B components on cultured cells.

EXAMPLE 6

In Vivo Assay (A) Animals

Male Balb/c mice were obtained from the National Laboratory Breeding Research Center in Taiwan and were raised in a specific pathogen-free environment. These mice used were between 6 and 8 weeks of age. Groups of six mice were caged separately according to their treatments. Recombinant *Dermatophoides pteronyssinus* group 2 (Der p 2) was prepared from Dr. Tsai's lab and test drugs, Traditional Chinese Medicine A (TCM-A, or 1217A in FIGS. 7, 8, 9, and 10) and Traditional Chinese Medicine B (TCM-B, or 1217B in FIGS. 7, 8, 9, and 10) were prepared from the Biomedical Engineering Center Industrial Technology Research Institute, Hsinchu, Taiwan.

(B) Induction of Allergic Airway Inflammation

Mice were immunized by intraperitoneal (i.p.) injection of 1 µg/0.1 ml Der p 2 emulsified in 4 µg/0.062 ml aluminum hydroxide $Al(OH)_3$ (Whitehall Lab Ltd, Punchbowel, Australia) on day 0 and day 7. After immunization, mice were fed with TCM for 3 weeks. Mice of different groups were fed with Dexamethasone (1 µg/mouse/day), TCM-A (20 mg/mouse/day), TCM-B (20 mg/mouse/day) or normal saline 500 µl/mouse/day. On days 28 and 35, mice were lightly anesthetized with an i.p. injection of 60 mg/kg of sodium pentobarbital (Sigma Chemical Co., St. Louis, Mo., USA) and intratracheally (i.t.) inoculated with 1 µg/50 µl of Der p 2. Twenty-four hours after the second i.t. inoculation, mice were sacrificed after pulmonary function measurement.

(C) Pulmonary Function Determination

Figure 5:
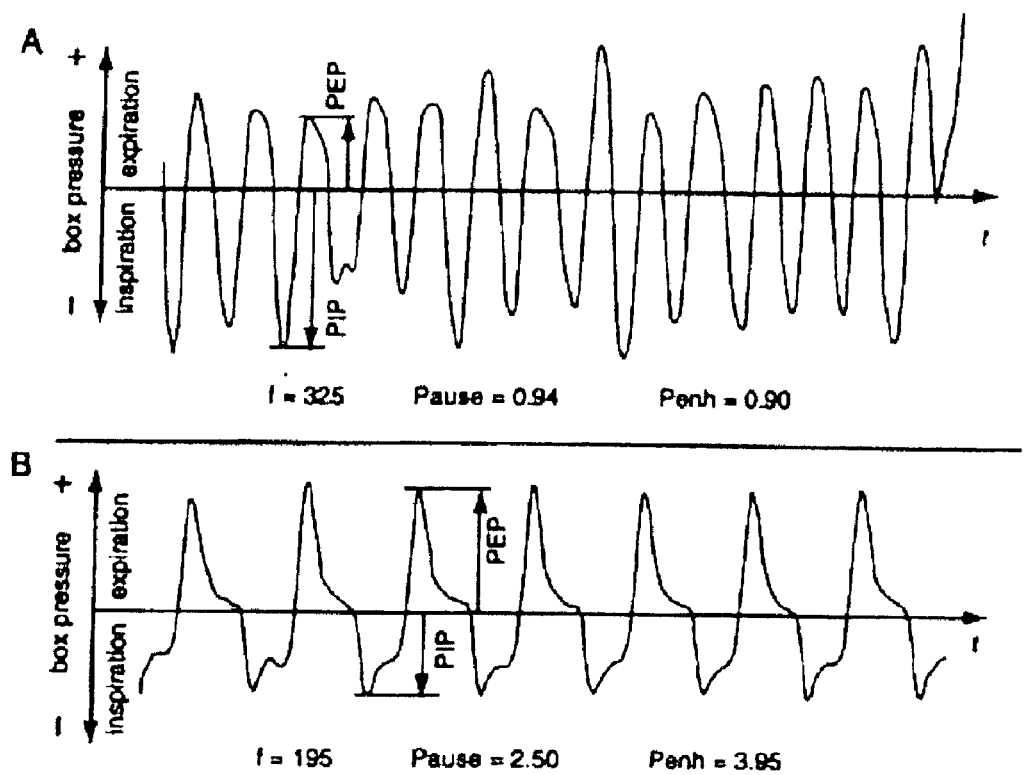
FIG. 5 shows the amplified pressure signal of the pulmonary function determination, wherein the increase of Penh value from 0.9 to 3.95 in (B) indicates deteriorated pulmonary function in the experimental allergic mouse, and is an example of different parameters being determined in mice (excerpted from E. Hamelmann and E. W. Gelfand in Current Protocols in Immunology, John Wiley & Sons, Inc., edited by J. E. Coligan, A. M. Kruisbeek, D. H. Margulies, E. M. Shevach, and W. Strober, Vol. 3, Chapter 15,18.1–18.13(1999))

Each mouse was placed inside a barometric plethysmograph (Buxco Electronics, Troy, N.Y.). The plethysmograph has two chambers: one is the main or animal chamber (ID 7.5 cm and 3.5 cm height) and the other one is the reference chamber (ID 7.5 cm and 3.5 cm height). A differential pressure transducer was employed to detect the pressure difference between the above two chambers. The pressure signal was amplified, digitized via an A/D convert card, and sent to a computer with a BioSystem XA program (Buxco Electronics, Troy, N.Y.), which sampled and calculated desired respiratory parameters. Similar to those reported by Hamelmann et al. (1997), parameters of enhanced pause (Penh), pause, tidal volume ($V_T$), breathing frequency (f), peak inspiratory flow (PIF), peak expiratory flow (PEF), end-inspiratory pause (EIP), and end-expiratory pause (EEP) were obtained, as shown in FIG. 5.

An aerosol was generated by placing a 5 ml saline or methacholine (1.56 to 50.00 mg/ml) solution in the cup of an ultrasonic nebulizer (DeVilbiss, Somerset, Pa.) and it was delivered via a connecting tube and a three-way connector to the animal chamber of the plethysmograph. The median size of the aerosol is approximately 3 µm; the range of the size is from 1 to 5 µm, according to the manufacturer's information. The aerosol usually filled the chamber within 15–20 sec. At first, each mouse inhaled the saline aerosol for 3 mins and then the respiratory parameters were measured for 3 mins. Then, inhalation of the saline aerosol was replaced by the aerosol of a methacholine solution for 3 mins. The aerosol in the chamber was cleared immediately after the exposure. Respiratory parameters were then measured for 3 mins following the inhalation of a methacholine aerosol. The dose-response curve for methacholine was performed starting from low dose to high dose. As shown in FIG. 5, sample TCM-B and Dexamethasone can improve the pulmonary function and immunological inflammation of allergic animals. There was a 15 min interval between any two different exposures. Values are means ±SEM. Differences in parameters among groups were analyzed with analysis of variance. If significant differences existed among groups, statistical differences between any two groups were analyzed by the Newman-Keuls test. Differences between values before and after saline or methacholine exposure were analyzed by a paired t-test. Differences between the saline control and the naïve groups were analyzed by an unpaired t-test. Differences were considered significant if p<0.05.

(D) Sample Collection and Preparation

Figure 6:
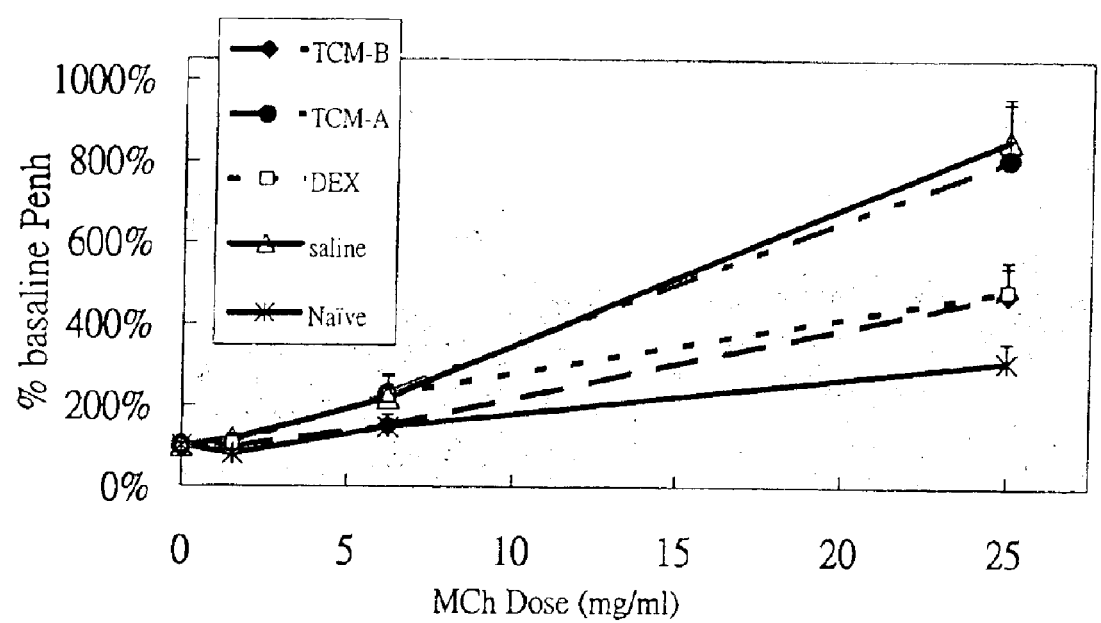
FIG. 6 shows that TCM-B can prevent the deteriorated pulmonary function induced by methacholine from low dose to high dose when compared normal saline treatment or TCM-B composition and its modifier to delete with *Rhizoma Alimatis* extract (TCM-A)

After pulmonary function measurement, bronchoalveolar lavage (BAL) was performed with the following procedure. Two separate injections of 1 ml sterile endotoxin-free saline were given into the lung via the trachea of each mouse. Approximately 1.8 ml of the bronchoalveolar lavage (BAL) fluid was recovered constantly. The BAL fluids were aspirated and stored at −70° C. until assay. After total leukocyte counting, a cytospin preparation of 100 ml BAL fluid was stained with Liu stain (Tonyar Diagnostic Inc, Taipei County, Taiwan) and differential counts were performed on 200 cells. The results are shown in FIG. 6 and Table 1 below. It is shown that the sample TCM-A and TCM-B can lower the inflammatory cells in the BAL fluids. Blood samples were obtained via the orbital sinus and sera were collected and stored at −70° C. until assay.

TABLE 1

| Sample | Total cell NO (×10⁴/ml) | Differential Counts(×10⁴/ml) | | | |
|---|---|---|---|---|---|
| | | Macro | Lym | Neu | Eos |
| Naïve | 14.3 ± 4.3* | 13.3 ± 4.3* | 1.0 ± 0.0* | 0 | 0 |
| Saline | 160.0 ± 23.5 | 56.4 ± 12.7 | 41.4 ± 6.5 | 36.8 ± 2.8 | 25.2 ± 4.5 |
| DEX | 46.4 ± 2.2* | 29.2 ± 4.4* | 9.4 ± 1.5* | 6.6 ± 1.0* | 3.2 ± 0.4* |
| TCM-A | 49.0 ± 3.7* | 25.8 ± 2.5* | 13.2 ± 1.8* | 6.0 ± 0.7* | 4.0 ± 0.7* |
| TCM-B | 41.6 ± 6.2* | 21.2 ± 2.6* | 10.2 ± 2.4* | 6.0 ± 1.2* | 4.2 ± 1.1* |

(E) Determination of Der p 2 Specific IgG1, IgG2a and IgE Antibodies

Figure 7:
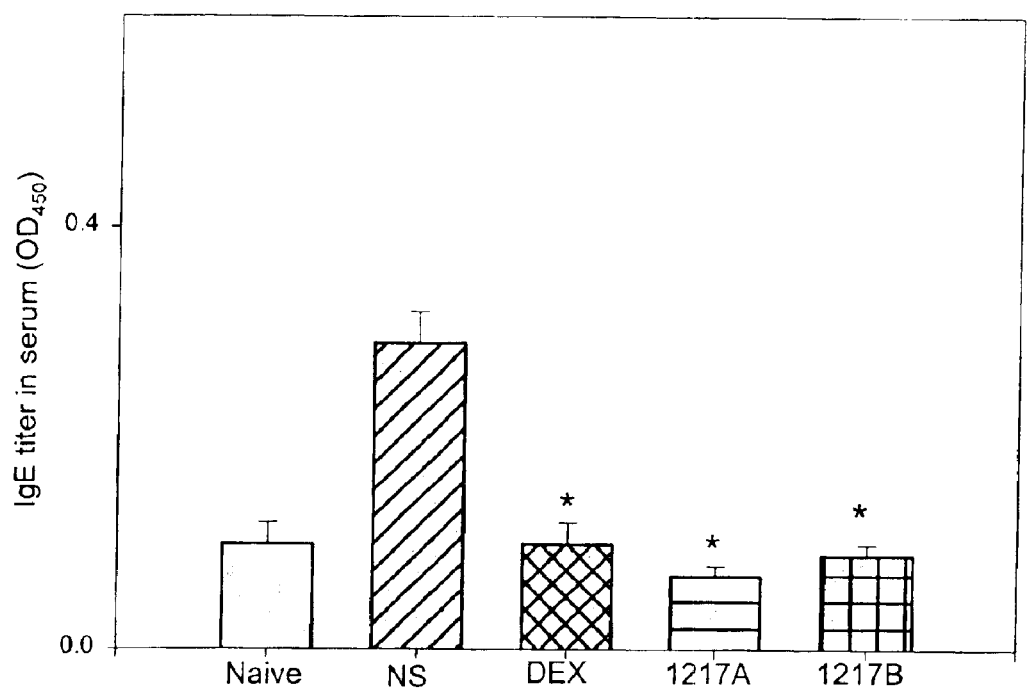
FIG. 7 is the graphic results showing the IgE titer in serum of the testing samples from five groups of mice.

Blood was obtained from retro-orbital venous plexus at the beginning and end of the experiment. Serum IgE IgG1 and IgG2a titer of anti-Der p 2 antibodies were determined by using an enzyme-linked immunosorbent assay (ELISA). Microtiter plates (Nunc Lab, IL, USA) were coated with 100 µl Der p 2 overnight at a concentration of 0.5 µg/ml in 4° C. refrigerator. Plates were washed with PBS-Tween-20 (PBST) three times and stored in −70° C. before use. After addition of 1:5 dilution for IgE, 1:100 dilution for IgG1 and 1:5 dilution for IgG2a of mice serum, plates were incubated for 4° C. overnight, then washed three times before the antibody (Horse radish peroxidase-conjugated goat anti-mouse IgE and IgG2a Ab 1:800, IgG1 Ab 1:2000, Southern Biotech Assoc, Inc, Birmingham, Ala., USA) was added. Following 1-hr incubation at 37° C. and three washes with PBST, the enzyme substrate ABTS [2,2"-Azion-bis(3-ethylbenzothiazolin-6-sulfonic acid) diammonium salt, Bio-Rad, USA] was added. The reaction was stopped with 50 µl 4N $H_2So_4$ after 15 mins and the optical density was measured at 450 nm in a multiscan spectrophotometer (model A-5682, SLT Lab Instruments, Salzburg, Austria). Results were expressed as ELISA units (EU). One EU was defined as the reciprocal value of the serum dilution that gave an optical density of 1.0. The result was always within the linear part of the dilution curve. To assure reproducibility, a known serum was run with each test as a standard. FIG. 7 is the IgE titer in serum of the testing samples.

(F) Cytokine Assays for Samples from Mice

Figure 8:
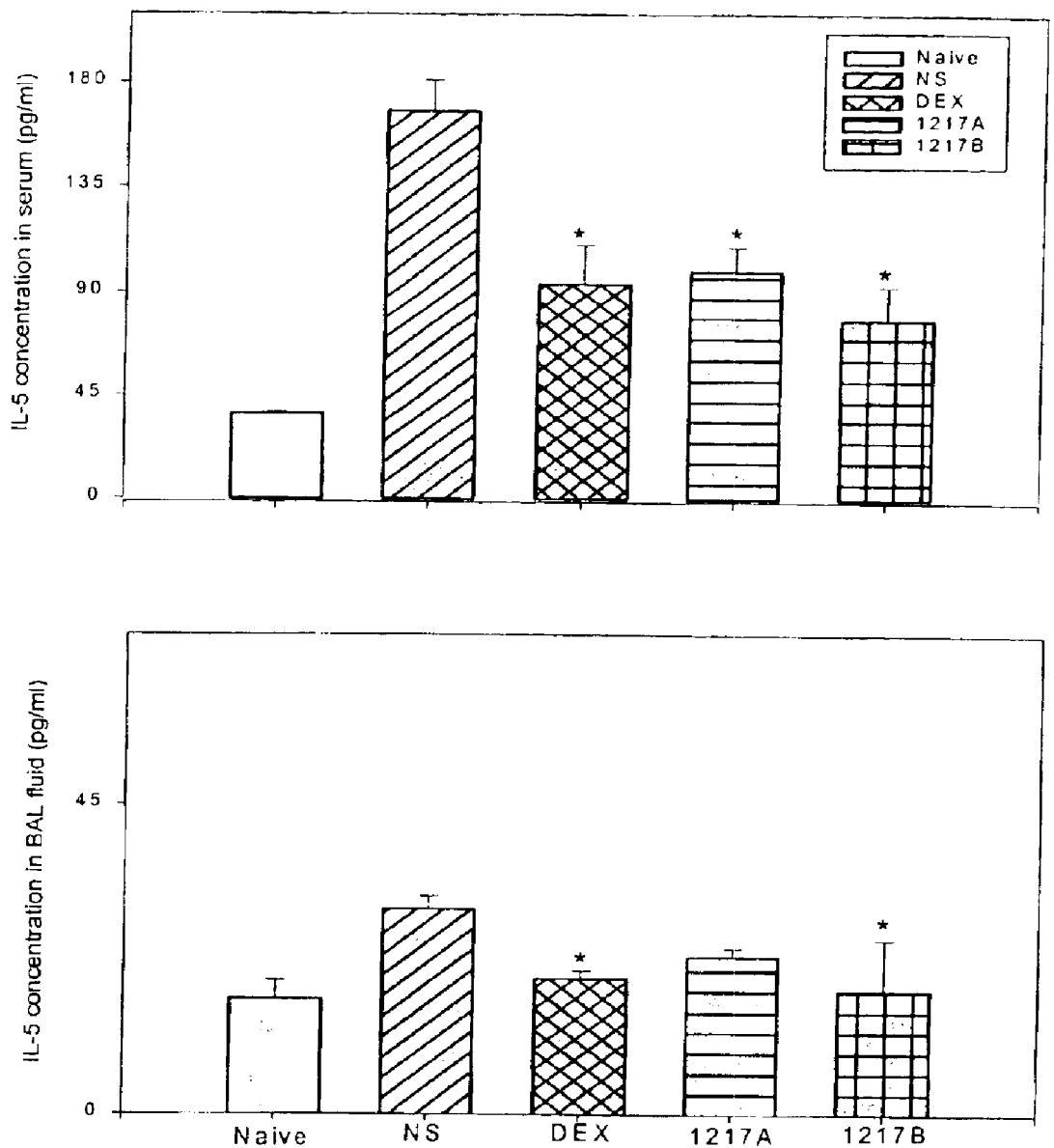
FIG. 8 is the graphic results showing IL-5 concentration in serum and in BAL fluid of the testing samples from five groups of mice.
Figure 9:
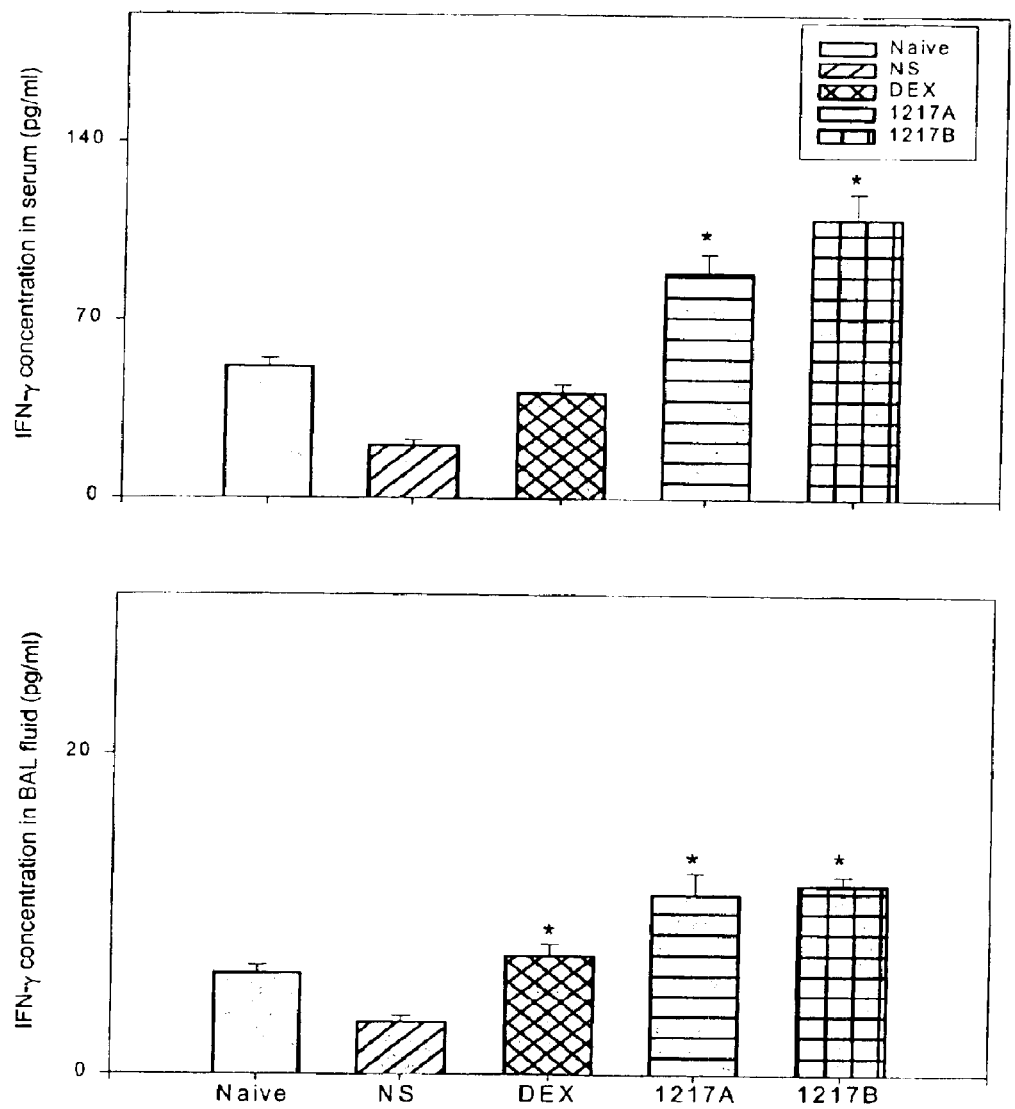
FIG. 9 is the graphic results showing IFN-γ concentration in serum and in BAL fluid of the testing samples from five groups of mice.

IFN-γ and IL-5 were measured by commercially available ELISA kits, using mouse monoclonal Ab recognizing different epitopes of the cytokine molecules. The lowest detector range was 10 pg/ml. The results are shown in FIGS. 8 and 9.

Figure 10:
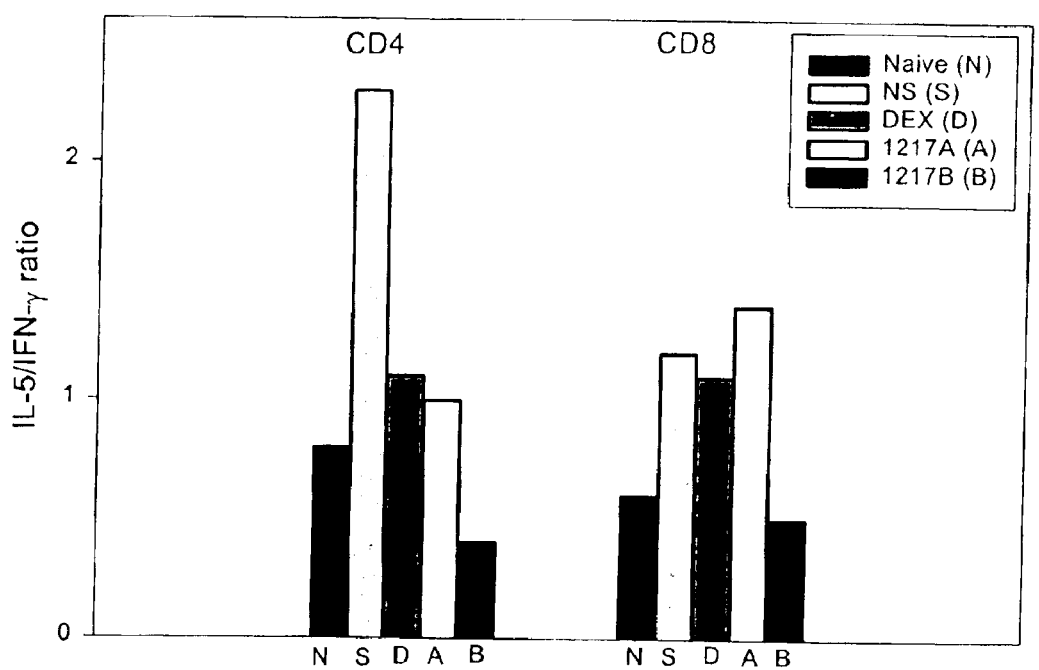
FIG. 10 is the graphic results showing that TCM-B (1217B) enhanced the regulation ability of T cells in blood of the testing samples from five groups of mice.

(G) Cell Culture of Bronchoalveolar Lavage Lymphocytes, Immunofluorescence Staining and Flow Cytometry Analysis Flow cytometric determination of cytokine in activated murine T helper cells was assayed according to the Assenmacher et al. (1994). Two-color staining methods were used to analyze IFN-γ and IL-5 expression in CD4 or CD8 cells. Leukocytes from peripheral blood (PBL) were stimulated with PMA (50 ng/ml), ionomycin (2 µM) and GolgiStop (Cytofix/Cytoperm Plus Cat No. 2076KK, Pharmingen, San Diego, Calif.) for 5-hrs and then washed twice by PBS. The cells were stained with CD4-FITC or CD8-FITC at room temperature (RT) for 30 mins and washed. Cells were fixed with cytofix/cytoperm at RT for 30 mins and stained with an anti-cytokine antibody at RT for 30 mins and washed. Cells were resuspended in 0.5 ml PBS containing 0.1% w/v sodium azide. Mean fluorescence was measured by Becton Diskinson flow cytometry (Becton Diskinson, CA, USA). A total of 2000 cells were analyzed in each sample. With reference to FIG. 10, there is shown a sample TCM-B that exhibited better regulation ability of T cells in blood.

(H) Statistical Analysis

Results were expressed as an arithmetic mean ±SEM. Differences among the groups were assessed by the Mann-Whitney U test. A P-value less than 0.05 was considered to be of statistical significance.

The aforesaid examples focus on evaluating the therapeutic effect of the pharmaceutical composition of the present invention. The preparation can resist airway allergic inflammation reaction, improve the pulmonary function, reduce IgE in bloods, and stop the asthma attack.

Although the present invention has been explained in relation to its preferred embodiment, it is to be understood that many other possible modifications and variations can be made without departing from the scope of the invention as hereinafter claimed. In other words, it is not intended to be limited to the details shown, since it will be understood that various omissions, modifications, subtractions and changes in the forms and details of the formulation illustrated and in its operation can be made by those skilled in the art without departing in any way from the spirit and scope of the present invention.

Without further analysis, the foregoing will so fully reveal the gist of the present invention that others can readily adapt it for various applications without omitting features that, from the standpoint of prior art, fairly constitute essential characteristics of this invention.

What is claimed is:

1. A pharmaceutical composition for treating allergic asthma comprising:

an alcoholic extract of *Radix Dioscorea;* an alcoholic extract of *Rhizoma Alismatis;* an alcoholic extract of *Poria cocos* (schw) Wolf; and an alcoholic extract of *Scutellaria Baicalensis;* wherein said alcohol used for extracting is alcohol solution to 95%, and the weight ratio of *Radix Dioscorea, Rhizoma Alismatis, Poria cocos* (schw) Wolf, and *Scutellaria Baicalensis* is 1–2:1–2:0.5–2:1–3 respectively.

2. The pharmaceutical composition as claimed in claim 1, wherein said extract of *Scutellaria Baicalensis* is extracted with an alcohol solution of 40% to 95%.

3. The pharmaceutical composition as claimed in claim 1, wherein each of said extracts of *Radix Dioscorea, Rhizoma Alismatis, Poria cocos* (schw) Wolf, and *Scutellaria Baicalensis* is separately extracted from *Radix Dioscorea, Rhizoma Alismatis, Poria cocos* (schw) Wolf, and *Scutellaria Baicalensis.*

4. The pharmaceutical composition as claimed in claim 1, wherein said extracts of *Radix Dioscorea, Rhizoma Alismatis, Poria cocos* (schw) Wolf, and *Scutellaria Baicalensis* are simultaneously extracted from the mixture of *Radix Dioscorea, Rhizoma Alismatis, Poria cocos* (schw) Wolf, and *Scutellaria Baicalensis.*

5. The pharmaceutical composition as claimed in claim 1 further comprising an excipient.

6. The pharmaceutical composition as claimed in claim 1, wherein said pharmaceutical composition is designed to treat patients with allergic asthma.

7. A method for preparing a pharmaceutical composition for treating allergic asthma composed of the extracts of *Radix Dioscorea, Rhizoma Alismatis, Poria cocos* (schw) Wolf, and *Scutellaria Baicalensis* comprising:

extracting *Radix Dioscorea, Rhizoma Alismatis, Poria cocos* (schw) Wolf, and *Scutellaria Baicalensis* in an alcohol separately to form extracts of *Radix Dioscorea, Rhizoma Alismatis, Poria cocos* (schw) Wolf, and *Scutellaria Baicalensis* to form alcohol extracts;

filtering and concentrating each of said extracts to form condensates of *Radix Dioscorea, Rhizoma Alismatis, Poria cocos* (schw) Wolf, and *Scutellaria Baicalensis;* and mixing said condensates of *Radix Dioscorea, Rhizoma Alismatis, Poria cocos* (schw) Wolf, and *Scutellaria Baicalensis* together;

wherein said alcohol used for extracting is alcohol of 40% to 95%, and the weight ratio of *Radix Dioscorea, Rhizome Alismatis, Poria cocos* (schw) Wolf, and *Scutellaria Baicalensis* is 1–2:1–2:0.5–2:1–3 respectively.

8. The method as claimed in claim 7, further comprising concentrating each of said condensates separately or together before drying together to form granules of *Radix Dioscorea, Rhizoma Alismatis, Poria cocos* (schw) Wolf, and *Scutellaria Baicalensis*.

9. The method as claimed in claim 7, further comprising adding an excipient to each of said condensates of *Radix Dioscorea, Rhizoma Alismatis, Poria cocos* (schw) Wolf, and *Scutellaria Baicalensis* before granulating.

10. The method as claimed in claim 7, wherein said granules are encapsulated.

11. A method for preparing a pharmaceutical composition for treating allergic asthma composed of the alcohol extracts of *Radix Dioscorea, Rhizoma Alismatis, Poria cocos* (schw) Wolf, and *Scutellaria Baicalensis* comprising: mixing *Radix Dioscorea, Rhizoma Alismatis, Poria cocos* (schw) Wolf, and *Scutellaria Baicalensis* to form a mixture;

extracting said mixture in alcohol to form an alcohol extract of *Radix Dioscorea, Rhizoma Alismatis, Poria cocos* (schw) Wolf, and *Scutellaria Baicalensis;* and filtering and concentrating said extract to form a condensate of *Radix Dioscorea, Rhizoma Alismatis, Poria cocos* (schw) Wolf, and *Scutellaria Baicalensis;* wherein said alcohol used for extracting is an alcohol solution to 95%, and the weight ratio of *Radix Dioscorea, Rhizoma Alismatis, Poria cocos* (schw) Wolf, and *Scutellaria Baicalensis* of said condensate is 1–2:1–2:0.5–2:1–3 respectively.

12. The method as claimed in claim 11, further comprising granulating said condensate by spray-drying to form a granule of *Radix Dioscorea, Rhizoma Alismatis, Poria cocos* (schw) Wolf, and *Scutellaria Baicalensis*.

13. The method as claimed in claim 11, further comprising adding an excipient carboxyl methylcellulose arid $Ca_3(PO_4)_2$ to said condensate of *Radix Dioscorea, Rhizoma Alismatis, Poria cocos* (schw) Wolf, and *Scutellaria Baicalensis* before granulating.

14. The method as claimed in claim 11, wherein said granule is encapsulated.

15. The method as claimed in claim 11, wherein said alcohol in said extracting is to 50% alcohol.

\* \* \* \* \*